United States Patent [19]

Tu

[11] 4,166,844

[45] Sep. 4, 1979

[54] SOLID PHASE SEPARATION TECHNIQUE FOR USE IN RADIOIMMUNOASSAYS

[75] Inventor: Jan-I Tu, North Brunswick, N.J.

[73] Assignee: E. R. Squibb & Sons, Inc., Princeton, N.J.

[21] Appl. No.: 788,477

[22] Filed: Apr. 18, 1977

[51] Int. Cl.² .................. A61K 43/00; G01N 33/16
[52] U.S. Cl. ................... 424/1; 23/230 B; 427/2; 435/7
[58] Field of Search ............ 424/1, 1.5, 12; 23/230 B; 427/2

[56] References Cited

U.S. PATENT DOCUMENTS

| | | | |
|---|---|---|---|
| 3,646,346 | 2/1972 | Catt | 424/12 |
| 3,720,760 | 3/1973 | Bennich et al. | 424/1 |
| 3,790,663 | 2/1974 | Garrison et al. | 424/12 |
| 3,904,367 | 9/1975 | Golibersuch | 23/230 B |
| 3,960,489 | 6/1976 | Giaever | 23/230 B |
| 3,979,509 | 9/1976 | Giaever | 424/12 |
| 4,017,597 | 4/1977 | Reynolds | 424/1.5 |
| 4,069,352 | 1/1978 | Parsons, Jr. | 424/1 |

OTHER PUBLICATIONS

Aach et al, Proc. Nat. Acad. Sci. USA, vol. 68, No. 5, May, 1971, pp. 1056–1060.

*Primary Examiner*—Leland A. Sebastian
*Attorney, Agent, or Firm*—Lawrence S. Levinson; Donald J. Barrack

[57] ABSTRACT

A radioimmunoassay procedure, and article of manufacture for carrying out that procedure, are disclosed herein. The solid phase separation technique utilized in the radioimmunoassay of this invention utilizes a test tube, the internal surface of which has been coated with two antibody layers.

4 Claims, No Drawings

SOLID PHASE SEPARATION TECHNIQUE FOR USE IN RADIOIMMUNOASSAYS

BACKGROUND OF THE INVENTION

The measurement of various body constituents by the use of radioimmunoassay techniques has achieved widespread acceptance in recent years. Exemplary of substances which can be measured by radioimmunoassay using currently available commercial kits are ACTH (adrenocorticotropin), aldosterone, angiotensin I, angiotensin II, barbiturates, cyclic AMP, cyclic GMP, digoxin, folic acid, FSH (follicle stimulating hormone), gastrin, $HB_sAg$ (hepatitis B antigen), HGH (human growth hormone), insulin, TSH (thyroid stimulating hormone), T4 (thyroxine), T3 (triiodothyronine), and vitamin B12.

Yalow and Berson, *In Vitro Procedures with Radioisotopes In Medicine*, International Atomic Energy Agency, Vienna (1970) pgs. 455 et seq., express the principle of radioimmunoassay in the following terms:

"Unlabelled antigen in unknown samples competes against labelled antigen ("tracer") for binding to antibody and thereby diminishes the binding of labelled antigen. The degree of competitive inhibition observed in unknown samples is compared with that obtained in known standard solutions for determination of concentration of antigen in unknowns."

The above-described type of radioimmunoassay procedure has come to be known as the "indirect" method of radioimmunoassay. Alternatively, the "direct" method of radioimmunoassay can be used to determine the presence or absence of a particular antigen in an unknown sample. In the "direct" method, labelled antibody is mixed with the unknown sample, which if it contains the antigen in question, will bind the labelled antibody.

In all radioimmunoassay procedures it is necessary to provide means for separating the bound from the free labelled tracer material. Many widely varied procedures have been developed and used; exemplary procedures are electrophoresis; chromatography; ion exchange; adsorption to dextran-coated charcoal, talc, or cellulose; and a number of solid-phase antibody techniques.

Two of the widely recognized solid-phase separation techniques comprise the covalent chemical bonding of an antibody to an insoluble polymeric substance or the physical adsorption of an antibody onto an insoluble polymeric substance; see, for example, Gurvich et al., *Nature*, 203:648 (1964); Wide et al., *Biochim. Biophys. Acta.*, 130:257 (1966); Catt et al., *Biochem. J.*, 100:31c (1966); Catt et al., *J. Lab. Clin. Med.*, 70:820 (1967); Catt et al., *Nature*, 213:825 (1967); Axen et al., *Nature*, 214:1302 (1967); Catt et al., *Science*, 158:1570 (1967); Wide et al., *Lancet*, 2:1105 (1967); Salmon et al., *J. Immunol.*, 103 (1):129 (1969); Catt, U.S. Pat. No. 3,646,346, issued Feb. 29, 1972; and Axen et al., U.S. Pat. No. 3,645,852, issued Feb. 29, 1972. The principal advantage of the solid-phase antibody separation techniques in radioimmunoassays is that they allow the isolation of bound from free labelled tracer material to be carried out by a relatively simple step at the completion of the immune reaction. This step may in practice, however, require several manipulations by the laboratory technician.

Catt's U.S. Pat. No. 3,646,346, issued Feb. 29, 1972, discloses an antibody-coated test tube as the means for carrying out a solid-phase separation. The tubes are prepared by adsorbing antibodies of the antigen to be tested on their internal surface. Adsorption is accomplished by incubating a buffered solution of the antibodies at room temperature for a period of several hours. Following the classical principles set down by Yalow and Berson, supra., a solution of labelled antigen and a solution of unlabelled antigen are incubated in the antibody-coated tubes causing the labelled and unlabelled antigens to compete for the available binding sites, and causing the formation of a two-phase system, i.e., a solid phase containing the bound antigen and a liquid phase containing the free antigen.

While the antibody-coated tube system has several advantages, it does have important drawbacks. Due to the unfavorable steric configuration of the antibody coated on the test tube, assay sensitivity is not as great as in some other systems. Furthermore, it is difficult, when preparing antibody-coated tubes, to maintain uniformity of the antibody coating from tube to tube.

Another solid-phase separation technique which has received recognition by the art is the double antibody solid-phase technique. The method is described by Parker in *Radioimmunoassay of Biologically Active Compounds* (1976), Prentice-Hall, Inc., Englewood Cliffs, New Jersey, pgs. 156–159 and by Hollander et al. in *Radioimmunoassay Methods* (1971), Churchill Livingston, Edinburgh, pgs. 419–422. The basic procedure comprises incubating a first antibody with labelled antigen and unlabelled antigen following the classical technique. Following the initial incubation a second antibody is added to the reaction system in an insolubilized form. This second antibody is of such a nature that it binds with the soluble antigen-antibody complex obtained in the first incubation to cause precipitation of the entire complex, i.e., antigen and double antibody. The second antibody is a nonspecific antibody and reacts with the antigen-antibody complex at sites on the more specific antibody which are non-reactive towards the antigen.

Parker, *Radioimmunoassay of Biologically Active Compounds, supra.,* at pg. 157, states that "In some systems preformed first antibody-second antibody complexes bind effectively to antigen, permitting a more rapid assay, albeit with some diminution in sensitivity."

Bosma et al., *J. Immunol.*, 115 (5):1381 (1975) deals with a solid phase radioimmunoassay that employs the "direct" method known as the sandwich technique. The technique of Bosma et al. comprises coating a plastic tube with a first coating of antigen followed by a second coating of divalent antibody. The antibody is chemically linked to the antigen with glutaraldehyde. The competitive reactions between labelled antigen and varying concentrations of unlabelled antigen are run in the coated tubes.

Immunochemical reactions have been used in tests for the determination of antigen or antibody other than radioimmunoassays; agglutination tests are exemplary. Schuurs' U.S. Pat. No. 3,551,555, issued Dec. 29, 1970, discloses the preparation of coated immunochemical reagent particles for use in agglutination reactions. According to the patent disclosure the reagent comprises finely divided solid carrier particles having adsorbed on the surface a protein inert to the determination method and next the antigen or antibody.

SUMMARY OF THE INVENTION

It is an object of this invention to provide an effective solid phase separation technique for utilization in the field of radioimmunoassays.

It is an object of this invention to provide a solid phase separation technique which provides high assay sensitivity.

It is an object of this invention to provide a solid phase separation technique which provides simplicity of operation for the technicians who utilize it.

These and other objects which will be apparent to persons of ordinary skill in the radioimmunossay field are accomplished by the radioimmunoassay method, and article of manufacture for carrying out that method, which are a part of this invention.

The solid phase separation technique of this invention is based on a test tube which has been coated on its internal surface with two antibody layers; a first layer of nonspecific antibodies which is bound, chemically or physically, to the internal surface of the test tube, and a second layer of more specific antibodies which are bound, chemically or physically, to the nonspecific antibodies.

The method of this invention for the qualitative or quantitative determination of an antigen comprises:

(i) Incubating a mixture of radioisotope-labelled antigen and unknown sample in a test tube which is coated with two layers of antibody; a first layer of nonspecific antibodies which is bound (chemically or physically) to the internal surface of the test tube, and a second layer of more specific antibodies which are bound (chemically or physically) to the nonspecific antibodies;

(ii) Separating the radioisotope-labelled antigen (and with it, of course, the unlabelled antigen) bound to the specific antibodies from the free radioisotope-labelled antigen (and unlabelled antigen);

(iii) Determining the radioactivity of the bound radioisotope-labelled antigen, the radioactivity of the free radioisotope-labelled antigen, or the radioactivity of each;

(iv) Referencing the amount of bound radioisotope-labelled antigen, the amount of free radioisotope-labelled antigen or the ratio of bound/free or free/-bound radioisotope-labelled antigen to corresponding values obtained by carrying out steps (i), (ii) and (iii) using as a sample known amounts of antigen; and (v) Determining the amount of antigen in the unknown sample using the relationship established in (iv).

DETAILED DESCRIPTION OF THE INVENTION

The double antibody-coated test tubes of this invention have at least a portion of their internal surface coated with two distinct layers of antibodies. The layer which is immediately adjacent to the surface of the tube is referred to hereinafter as the layer of nonspecific antibodies. By "nonspecific" is meant that the antibodies will be substantially non-binding with the antigen being tested. The layer of antibodies which is bound to the nonspecific antibodies will hereinafter be referred to as the layer of specific antibodies. By "specific" is meant that the antibodies will bind with the antigen unknown. Methods for preparing both specific and nonspecific antibodies are well known in the literature. The nonspecific antibody may be obtained by the immunization of a species (other than the species used to obtain the specific antibody) with purified nonspecific gamma globulin obtained from the species serving as the source of the specific antibody.

The test tubes themselves may be described as the conventional laboratory test tubes. Polystyrene has been found to be a particularly acceptable material for the test tubes of this invention. However, many other polymeric materials such as polyethylene, polypropylene, polycarbonate, ethylene-tetrafluoroethylene copolymer, and others may be used. The material must be capable of binding, physically or chemically, the layer of nonspecific antibodies. While this invention is being described in terms of double antibody-coated test tubes, it will be apparent to a person of ordinary skill in the radioimmunoassay art that various receptacles will be equivalent to the test tubes. For example, each well of a receptacle tray with multiple wells can be coated with a double layer of antibodies instead of using multiple test tubes.

Preparation of the double antibody-coated test tubes involves two distinct procedures; coating of the tubes with nonspecific antibodies and subsequent coating of the nonspecific antibody-coated tubes with specific antibodies. Prior treatment of the tubes with aqueous sodium chloride improves the uniformity of the nonspecific antibody coating. It is contemplated that each of the coating procedures may be carried out by either physical adsorption or by chemical reaction. Physical adsorption of the antibody layer can be achieved, for example, by merely agitating a buffered solution of the antibody in the test tube (or in the test tube already coated with the non-specific antibody); see, for example, Catt et al., *Science,* 158, 1570–1572 (1967). Chemical linking of the non-specific antibody to the internal surface of the test tube, or of the specific antibody to the nonspecific antibody, is also possible if the tube is made of a polymeric material with reactive functional groups or if functional groups can be added to the polymeric material. It has been found to be particularly beneficial to adsorb the nonspecific antibody to the test tubes and to chemically link the specific antibody to the nonspecific antibody.

The chemical linking of one antibody layer to another may be accomplished using glutaraldehyde. A buffered solution of specific antibody is first added to the test tube which has been previously coated with the nonspecific antibody and incubated at a reduced temperature, preferably about 2°–8° C., for a period of at least 18 hours. The tube is then aspirated and a buffered solution of bovine serum albumin is added to the tube which is aspirated immediately. Additional buffered bovine serum albumin solution is added to the tube and this time it is incubated for at least one hour at a reduced temperature of about 2°–8° C. before aspirating. The bovine serum albumin serves to stabilize the specific antibody by maintaining it in the proper steric configuration. It prevents denaturation of the antibody, allowing it to maintain its natural configuration. Following the final aspiration of the tube to remove the bovine serum albumin buffered solution, a buffered solution of glutaraldehyde is incubated in the tube for about one hour at a reduced temperature, preferably about 2°–8° C. The glutaraldehyde is a bi-functional reagent which, it is believed, specifically reacts with the epsilon-amino groups of a lysyl residue and thus creates a chemical bond between the nonspecific and specific antibodies through their lysine moieties. After aspirating the buffered glutaraldehyde solution, the tube is again washed quickly with a buffered solution of bovine serum albumin, and then, with a second buffered bovine serum albumin solution, allowed to stand at a reduced temperature, preferably at about 2°–8° C., for at least one hour. The tube is then aspirated and air dried at a reduced temperature, preferably about 2°–8° C.

Double antibody-coated tubes of the above-described type may serve as an integral part of a kit which can be used for the qualitative or quantitative determination by radioimmunoassay of a particular antigen. In addition to the coated tubes, the kit should contain a supply of radioisotope-labelled antigen and a supply of unlabelled antigen of known concentration. If only one vial of unlabelled antigen is supplied as part of the kit, it will be necessary for the user of the kit to make up several working solutions of unlabelled antigen of varying concentrations (or to add varying amounts of the single concentration to different tubes). It is, of course, more convenient for the user if the kit contains several vials of unlabelled antigen of varying concentrations. The kit may optionally contain an antigen control serum. This is a solution of known concentration of antigen in dehormonized serum and is used as an assay control.

The double antibody-coated test tubes described above are an integral part of the radioimmunoassay test procedure of this invention. The procedure comprises incubating a mixture of radioisotope-labelled antigen and a sample (containing a known or unknown concentration of antigen) in a double antibody-coated test tube. In the practice of this invention, it will be convenient to incubate many tubes at the same time. Some of the tubes will contain unknown samples (i.e., the fluid to be tested) and some of the tubes will contain known concentrations of the antigen being tested for. Incubation times will vary according to the particular test. Various radioisotopes may be used to label the antigen tracer; iodine-125 and iodine-131 are the most common labels.

During the incubation period a two-phase system forms in each of the test tubes. The phases are: (i) a solid phase comprising the bound antigen (labelled and unlabelled) linked to the test tube through the double antibody system, and (ii) a liquid phase containing the free antigen (labelled and unlabelled). Separation of the phases may be accomplished using any one of a number of procedures, e.g., aspiration or decantation. The specific manipulations required for the separation will depend on whether the practitioner of this invention elects to determine the radioactivity of the solid phase (bound antigen), liquid phase (free antigen) or of both phases. Clearly, if only the radioactivity of the solid-phase is being determined, the liquid phase need not be accurately collected.

After the solid and liquid phases contained in each tube are separated, the amount of radioisotope-labelled antigen (i.e., the level of radioactivity) in either or both phases is determined using art-recognized procedures. The amount of antigen in each of the unknown samples can be determined by referencing the amount of radioisotope-labelled antigen in either phase (or a ratio of the amounts in each phase) resulting from incubation of the unknown sample, to corresponding values obtained using known concentrations of antigen. The "referencing" procedure can be conveniently carried out by preparing a graph of radioactivity levels versus concentration of antigen.

The following is a detailed (although generalized) description of a test procedure of this invention utilizing a kit comprising the following components:
 (a) Radioisotope-labelled antigen
 (b) Antigen standards of concentrations 0, 0.5, 1.0, 2.0, 3.0 and 5.0, nanograms of antigen per milliliter.
 (c) Antigen control serum of known concentration
 (d) Double antibody-coated polystyrene test tubes The procedure is as follows:
1. Mark a series of antibody-coated tubes with the numbers 1 through 16. The first 12 tubes are required for the standard curve, tubes 13 and 14 for control serum, and tubes 15 and 16 for the test sample.
2. 
 Add 50 μl of 0 ng Standard to tubes 1 and 2.
 Add 50 μl of 0.5 ng Standard to tubes 3 and 4.
 Add 50 μl of 1.0 ng Standard to tubes 5 and 6.
 Add 50 μl of 2.0 ng Standard to tubes 7 and 8.
 Add 50 μl of 3.0 ng Standard to tubes 9 and 10.
 Add 50 μl of 5.0 ng Standard to tubes 11 and 12.
3. 
 Add 50 μl of Control Serum to tubes 13 and 14 and add 50 μl of Test Sample to tubes 15 and 16.
4. 
 Add 1 ml of radioisotope-labelled antigen solution to all tubes.
5. Shake the tubes gently by hand to mix the contents.
6. Incubate.
7. Aspirate or decant the contents of all tubes.
8. Wash each tube with 1 ml of normal saline.
9. Place 1 ml of radioisotope-labelled antigen in two plastic tubes (not coated) marked as total count tubes.
10. Count all tubes for 1 minute in a suitable well counter.

Calculations

1. Calculate the average counts per minute (cpm) for each set of duplicate tubes.
2. Calculate the % Binding for the '0' ng tube as follows:

$$\% \text{ Binding for '0' } ng = \frac{100 \times \text{ave } CPM \text{ for '0' } ng \text{ tubes}}{\text{Average } CPM \text{ for Total Count Tubes}}$$

3. Calculate $B/B_0$ Values for each set of tubes where
 B = Average CPM for a given set of tubes and
 B = Average CPM for '0' ng tubes
NOTE: The $B/B_0$ Value for the '0' ng tube, therefore, will always be 1.0.
4. Prepare a Standard Curve on a graph paper using $B/B_0$ values on the vertical axis and 'ngs' on the horizontal axis.
5. Determine the quantity (ng/ml) of antigen in the Control Serum Test Sample by referring to the Standard Curve.
6. Determine the quantity of antigen in the test sample by referring to the Standard Curve.

The following examples are specific embodiments of the double antibody-coated test tubes of this invention.

EXAMPLE 1

Preparation of double antibody-coated test tubes for use in radioimmunoassay for determination of plasma digoxin levels Polystyrene test tubes (12×75 mm) are treated with aqueous sodium chloride solution and then washed repeatedly with water.

Goat anti-rabbit globulin (obtained by immunizing goats with purified nonspecific gamma globulin obtained from rabbits) in buffer solution of sodium carbonate and sodium bicarbonate is added to each of the test tubes at room temperature and incubated for about 18 hours at a temperature of 2°–8° C. The goat anti-rabbit globulin solution is aspirated from the tubes and a solution of bovine serum albumin (at 2°–8° C.) in tris-acetate buffer (prepared from tris(hydroxymethyl)aminomethane and glacial acetic acid) is added, and incubated at 2°–8° C. for about 1 hour. The tubes are then aspirated, air-dried, and maintained at 2°–8° C.

Digoxin antibody (obtained by the immunization of rabbits) is mixed with a tris-acetate buffered solution of bovine serum albumin, added to the test tubes and incubated at 2°–8° C. for about 18 hours. The tubes are aspirated, and washed with a tris-acetate buffered solution (at 2°–8° C.) of bovine serum albumin. Tris-acetate buffered solution of bovine serum albumin is again added to the test tubes which are incubated for about 1 hour at 2°–8° C., and aspirated. A tris-acetate buffered solution of glutaraldehyde is added to each tube, which is incubated at 2°–8° C. for about 1 hour, and then aspirated. Tris-acetate buffered solutions of bovine serum albumin are used to wash the tubes, which are stored at 2°–8° C.

EXAMPLE 2

Preparation of double antibody-coated test tubes for use in radioimmunoassay for determination of serum triiodothyronine (T3)

Polystyrene test tubes (12×75 mm) are treated with aqueous sodium chloride solution and coated with goat anti-rabbit globulin as described in Example 1.

T3 antibody (obtained by the immunization of rabbits) is mixed with a tris-acetate buffered solution of bovine serum albumin, added to the test tubes and incubated at room temperature for about 18 hours. The tubes are aspirated, and washed twice with a tris-acetate buffered solution of bovine serum albumin (at 2°–8° C.) After making certain that the buffer is completely removed from the test tubes, a tris-acetate buffered solution of glutaraldehyde (at 2°–8° C.) is added to the test tubes, incubated at 2°–8° C. for about 1 hour, and aspirated. Tris-acetate buffered solutions of bovine serum albumin are used to wash the tubes, which are stored at 2°–8° C.

What is claimed is:

1. A double antibody-coated test tube comprising a test tube capable of binding a layer of antibodies, having bound to at least a portion of its internal surface a layer of nonspecific antibodies and having bound to the layer of nonspecific antibodies a layer or specific antibodies, wherein the layer of specific antibodies is chemically linked to the layer of nonspecific antibodies.

2. A double antibody-coated test tube in accordance with claim 1 wherein the layer of nonspecific antibodies is physically adsorbed on the test tube.

3. A double antibody-coated test tube in accordance with claim 1 wherein the test tube is made of polystyrene.

4. A process for the determination of an antigen unknown comprising:
   (i) incubating a mixture of radioisotope-labelled antigen and unknown sample in a double antibody-coated test tube comprising a test tube capable of binding a layer of antibodies, having bound to at least a portion of its internal surface a layer of antibodies that is substantially non-binding with the antigen unknown, and having chemically linked to the first layer of antibodies a second layer of antibodies, the antibodies in said second layer being capable of binding with the antigen unknown;
   (ii) separating the radioisotope-labelled antigen bound to the double antibody-coated test tube from the free radioisotope-labelled antigen;
   (iii) determining the radioactivity of the bound radioisotope-labelled antigen, the radioactivity of the free radioisotope-labelled antigen or the radioactivity of each;
   (iv) referencing the amount of bound radioisotope-labelled antigen, the amount of free radioisotope-labelled antigen or the ratio of bound/free or free/bound radioisotope-labelled antigen to corresponding values obtained by carrying out steps (i), (ii) and (iii) using as a sample known amounts of antigen; and
   (v) determining the amount of antigen in the unknown sample using the relationship established in (iv).

* * * * *

UNITED STATES PATENT AND TRADEMARK OFFICE
CERTIFICATE OF CORRECTION

PATENT NO. : 4,166,844
DATED : September 4, 1979
INVENTOR(S) : Jan I. Tu

It is certified that error appears in the above-identified patent and that said Letters Patent are hereby corrected as shown below:

In column 8, line 8, please delete the word "or" and replace it with the word --of--

Signed and Sealed this

Sixteenth Day of September 1980

[SEAL]

Attest:

SIDNEY A. DIAMOND

Attesting Officer   Commissioner of Patents and Trademarks